United States Patent [19]

Dance et al.

[11] Patent Number: 5,273,526
[45] Date of Patent: Dec. 28, 1993

[54] VASCULAR OCCULUSION REMOVAL DEVICES AND METHOD

[75] Inventors: Creg W. Dance; John Vanden Hoek, both of Elk River; Victor R. Blackledge, Chaska, all of Minn.

[73] Assignee: Lake Region Manufacturing Company, Inc., Chaska, Minn.

[21] Appl. No.: 719,314

[22] Filed: Jun. 21, 1991

[51] Int. Cl.$^5$ ............................................. A61M 1/00
[52] U.S. Cl. .................................................. 604/35
[58] Field of Search ............... 604/35, 28, 27, 22; 606/159

[56] References Cited

U.S. PATENT DOCUMENTS

| | | | |
|---|---|---|---|
| 4,664,112 | 5/1987 | Kensey et al. | 606/159 X |
| 4,747,821 | 5/1988 | Kensey et al. | 604/22 |
| 4,749,376 | 6/1988 | Kensey et al. | 604/22 |
| 4,795,438 | 1/1989 | Kensey et al. | 604/22 |
| 4,950,238 | 8/1990 | Sullivan | 606/159 X |
| 5,114,399 | 5/1992 | Kovalcheck | 606/159 X |

FOREIGN PATENT DOCUMENTS 0232678 8/1987 European Pat. Off. ............ 606/159

*Primary Examiner*—Cary E. O'Connor
*Assistant Examiner*—Jeffrey A. Smith
*Attorney, Agent, or Firm*—Grady J. Frenchick

[57] ABSTRACT

A catheter for removing vascular obstruction(s) is disclosed. The catheter employs a configuration comprising generally coaxial, rapidly rotatable drive cable, fluid output lumens or channels, and fluid input lumens or channels. The drive cable is fixedly coupled to an elongate head so as to permit the head to be rapidly rotated by the drive cable. The head includes flats or impellers which, when rapidly rotated, generate a zone of turbulence or a vortex adjacent the vascular obstruction. The turbulence generated by the device tends to break up or dismantle the obstruction. The fluid input and output mechanisms permit fluid to be delivered to the vicinity of the obstruction and debris from the obstruction to be removed.

In a preferred practice, a catheter of the invention is hollow, permitting it to be slid over a guide wire which has been steered to the site of the vascular obstruction. The distal end of the catheter, specifically the head, is steered to a location adjacent the obstruction by utilization of the guide wire.

Methods for removing vascular obstructions are disclosed. Preferably, pulsatile turbulence generation is employed.

34 Claims, 7 Drawing Sheets

VASCULAR OCCULUSION REMOVAL DEVICES AND METHOD

BACKGROUND OF THE INVENTION

1. Field of the Invention

This invention relates to vascular occlusion removal or thrombus dissolution or destruction devices. More specifically, this invention relates to thrombus dissolution devices or catheters for insertion in body vessels for removing obstructions therefrom. Yet more specifically, this invention relates to apparatuses or thrombectomy devices for removing vascular obstructions such as thrombi by the creation of turbulence or a vortex near or adjacent to an obstruction or occlusion. Concurrently or subsequently, suction or aspiration removal of the resulting disintegrated obstruction material is described.

2. Description of the Prior Art

The removal of harmful blockages from vessels, ducts or passages within the body is typically accomplished by one of several techniques. One technique utilizes a treatment catheter equipped with two inflatable balloons. The inflatable balloons are used to seal off a constricted area in a duct or passage such as a blood vessel. An inlet member is provided within the catheter for supplying a suitable solvent, such as a thrombolytic agent or solution of digestive enzymes, to the area delimited by the two balloons. An outlet member is provided for removing the dissolved material from the site of the restriction. In addition, a second supply channel is provided for allowing the blood or other body fluid to bypass the delimited area, thus preventing a complete vascular or coronary obstruction. A second technique, balloon angioplasty, involves deployment of a balloon catheter within the obstructed vessel so that, when the balloon is inflated, the constriction or obstruction material is compressed against the vessel walls.

A problem with the above techniques is that they may cause blood vessel wall damage.

Another more recent technique, known as laser angioplasty, uses laser energy to vaporize an obstruction. In this technique, the catheter, which is mounted for rotation and translation about a filament, has a pair of abutments disposed on its distal end. Also included on the distal end of the catheter is a bladder which, when inflated, causes the abutments to bear against the inner surface of the blood vessel so that the space between the abutments defines a working chamber for delimiting the area around an obstruction. A fiber optic connected to a source of laser energy extends through the catheter, with the distal end of the fiber optic being disposed in one of the abutments. In addition, a suction port is provided between the abutments for removing disintegrated material from the delimited area. Severing means such as a blade or a heated element also may be included for severing and releasing material which is not vaporized by the laser. As with balloon angioplasty, laser angioplasty can result in damage to the blood vessel itself.

Another technique for removal of blockages utilizes what is generally referred to as an atherectomy device or catheter. An example of this type of device is disclosed in U.S. Pat. No. 4,631,052 to Kensey. The Kensey '052 patent device comprises a bladed cutting head which is rotated by a turbine drive to cut away occlusions in a body vessel. This Kensey '052 catheter presents the possibility of vessel wall damage if its rotary head were to be deflected by an especially hard portion of an occlusion.

U.S. Pat. No. 4,950,238 issued to Dennis E. Sullivan describes a hydro-rotary vascular catheter which is a variation on the balloon angioplasty technique described above. Sullivan discloses a catheter having a rotary, fluid-directing head and isolation means, e.g., balloons, which are positioned upstream and downstream of the obstruction. After being positioned, the upstream and downstream balloons are inflated with the patient's blood and a pressurized flushing fluid, respectively, to seal off the obstruction. Flushing fluid is ejected from the rotary fluid-directing head of the Sullivan catheter which causes the head to rotate. This rotation creates turbulence which, in conjunction with the fluid streams themselves, is said to break down the vessel obstruction. A return channel permits debris to be removed from the constricted area. The Sullivan device is structurally complicated and has the admitted drawback of occasionally requiring the use of digestive enzymes or other solvents such as those used in some forms of vascular treatment discussed above.

U.S. Pat. No. 4,749,376, to Kenneth Kensey et al. discloses a "Reciprocating, Working Head Catheter". The catheter of Kensey et al. comprises an elongated drive wire extending through the catheter body and a motion transtator located at the distal end of the catheter. The drive wire is rotated at high speed and the transtator translates the rotary motion into reciprocating motion. In this manner the working head is rotated and reciprocated. This motion, in conjunction with a fluid, permits the catheter to open the body vessel in which it is inserted. No aspiration or removal of debris is disclosed or suggested in the Kensey et al '376 patent.

U.S. Pat. No. 4,445,509 to David C. Auth discloses a rotating head cutting tool recanalization catheter having spirally shaped cutting flutes with hardness-differential cutting properties. Plaque and other obstructions are alleged to be removed from organic structures without damage to normal tissue. The cutting apparatus of the Auth et al. patent is disclosed to be rapidly rotated within the blood vessel of a patient by means of an external torque-generating device, e.g., an electric motor. In operation, then, the cutting tool is advanced against a blood vessel lesion or obstruction and the obstruction is differentially cut. The apparatus of Auth et al. has a fluid port in communication with an external suction device so that blood and debris from the cutting operation can be removed from the cutting site.

U.S. Pat. No. 4,631,052 to Kenneth R. Kensey discloses a rotating head or recanalization catheter which is advanced through the body passageways to the site of a restriction. The apparatus of the Kensey '052 patent is disclosed to operate by cutting or by mechanically beating or otherwise agitating or disturbing the blockage material to form an opening. A perfusion structure is provided which provides oxygenated fluids, drugs, contrast media or dyes into the occluded or blocked passage way.

U.S. Pat. No. 4,795,438 also to Kenneth Kensey discloses a method and apparatus for forming a restriction in a vessel, such as a fallopian tube. No removal of unwanted vascular obstructions is disclosed or contemplated in the Kensey '438 patent.

U.S. Pat. No. 4,784,636 to Mark A. Rydell discloses a balloon atherectomy catheter. The Rydell '636 patent apparatus has an angular cutting tip fixed to the distal end of an elongated drive tube. A separate rotational drive mechanism is coupled to the drive tube to rotate the drive tip. Provision is made for introducing fluid through the loop of the guide catheter for inflating the balloon and for aspirating blood and loose particles away from the occlusion site. The balloon mechanism is used primarily to retain the distal end of the catheter assembly in place near the occlusion to permit the cutting operation to be performed.

U.S. Pat. No. 4,715,538 to Horst Lingnau and U.S. Pat. No. 3,120,326 to Ernie D. Willhoite disclose jet nozzles and rotary spray devices, respectively. The inventions of Lingnau and Willhoite are useful for cleaning narrow tubular parts, such as pipes, or for drilling though soft materials by means of jet or spray nozzles. These references make no mention of possible medical applications of these inventions.

Recently, a catheter has been described which comprises a distal end header in fluid communication with a plurality of proximal end- or backward-directed high pressure jets. Fluids are fed to the header through the body of the catheter by means of an off-center input pipe or lumen. The high pressure jets direct fluid backward away from the thrombus, and thereby create a vortex which allegedly tends to remove it. No rotation of the header is possible.

None of the above patents alone or in combination disclose or suggest the invention of the present application.

BRIEF SUMMARY OF THE INVENTION

Briefly, in one aspect, the present invention is a catheter for removing an obstruction in a body vessel which generally involves no cutting or mechanical destruction of the obstruction or deposit. A device of this invention effectuates removal of the obstruction or deposit by the creation of fluid turbulence or a vortex in the region immediately adjacent the obstruction. Aspiration of the resulting detritus or debris, to remove it from the obstruction site, is contemplated. By application of this invention, an obstruction is removed from the vessel without injury or damage to the surrounding vessel walls. In most instances there is no need for physical contact between the obstruction and any part of this invention in order for the vessel obstruction to be destroyed and removed.

A catheter of the present invention comprises a flexible, tubular, or elongate sleeve or catheter body having distal and proximal ends. The sleeve, catheter body, or external sheath has drive means extending therethrough so as to project from the distal end. The drive means, such as a drive cable or drive wire, can be utilized to assist in guiding or pushing the catheter through the torturous path of the vessels of a body to a point where the distal end of the catheter, e.g., the head means, is located near the obstruction. As such, the drive means is both flexible and, preferably, steerable. The drive means of the present invention must be rapidly rotatable within the catheter body. The drive means also comprises a head means or a tip fixedly mounted on its projecting end.

The head means comprises a substantially smooth, bulbous or ellipsoid head having a base or neck. The head means is mounted on the drive means at the base of the head so as to be rapidly rotated thereby. The head means generally includes a turbulence or vortex generating means. The turbulence generating means generally is disposed at the base or neck of the head between the distal end of the catheter body and the head itself. A turbulence generating means of this invention, such as a plurality of facets, veins, impellers, or flats, is disposed at or adjacent the base of the head so as to create turbulence when the drive means, and hence the head means, is rapidly rotated, e.g., by an external source of rotational energy such as an electric motor or compressed air.

A catheter of the present invention further comprises means for delivering a fluid or fluids proximate the turbulence generating means and fluid and debris or detritus recovering means also located proximate the turbulence generating means. The fluid delivery and recovery means can be used to deliver and retrieve essentially any fluid material to the distal, working end of the catheter. The fluid recovering means permits debris and particles generated from the obstruction to be easily and conveniently removed from the site thereof. The fluid delivery and fluid recovery means may be operated simultaneously or sequentially.

The fluid delivery and recovery means of the invention further comprise channels, lumens, input and output orifices or ports. The channels are generally coaxial and run through the catheter body within the sleeve. Sources of pressurized fluid, usually external, are contemplated. The debris recovery means also generally includes an external vacuum source or an aspirator.

In a preferred practice, a device of the present invention is constructed so as to permit it to be used with a guide means such as a guide wire. Guide wires, especially steerable guide wires, are used to lead the catheter to a previously identified obstruction site. Using conventional techniques, a guide wire is steered or directed through the operant vessel and its distal end or tip is located adjacent the vessel obstruction. A catheter of this invention then is slid over the guide wire to the point where the head means also is located adjacent the obstruction, overlapping or in contact with the distal tip or end of the guide wire. Guide wires may be treated, e.g., by coating with slippery materials, to make the sliding process easier. If used with a guide wire, a device of this invention will be hollow comprising an inner hollow lumen, of approximate guide wire diameter, which permits the catheter easily to slide over the guide wire to the location of the vascular obstruction once the distal tip of the guide wire has been steered thereto.

In a method of the present invention, the location of a vascular or vessel obstruction is identified. The distal end of a catheter of the above structure is steered to the a location adjacent to, or near the previously-located obstruction, preferably using a guide means as described above. The distance between the distal end of the catheter, i.e., the head means, and the obstruction should permit the turbulence generated by the turbulence generating means, preferably in conjunction with fluid delivery, to impact and erode the obstruction. The catheter, via the drive means, is then connected or coupled to external rotation means, external debris removal means, e.g., an aspirator, and external fluid input means, e.g., a pump. The drive means then is rapidly rotated by the external rotation means simultaneously or in conjunction with delivery of pressurized fluid adjacent to the site of the obstruction and proximate to the turbulence generating means. The pressurized incoming or input fluid can interact with, or impinge upon, the turbulence generating means to create a vortex or zone of turbulence which tends efficiently to remove the obstruction without damaging vessel structures. The external debris removal means (e.g., suction) may be simultaneously or subsequently activated so as to remove particles generated from the obstruction by the turbulence. In this manner, removal of the vessel obstruction, and especially debris therefrom, is accomplished. It will, of course, be necessary for the rates of output and input of the fluid input means and the debris recovery means to be adjusted so that the body vessel is neither collapsed nor expanded.

Throughout the description of the present invention, the terms "vessel" or "body vessel" are intended to be broadly construed to include essentially any vessel, including veins and arteries, whether they are of a coronary or peripheral nature. Moreover, while specifically directed toward human body vessels, removal of obstructions from essentially any body vessel is contemplated herein.

DETAILED DESCRIPTION OF THE INVENTION

Figure 1:
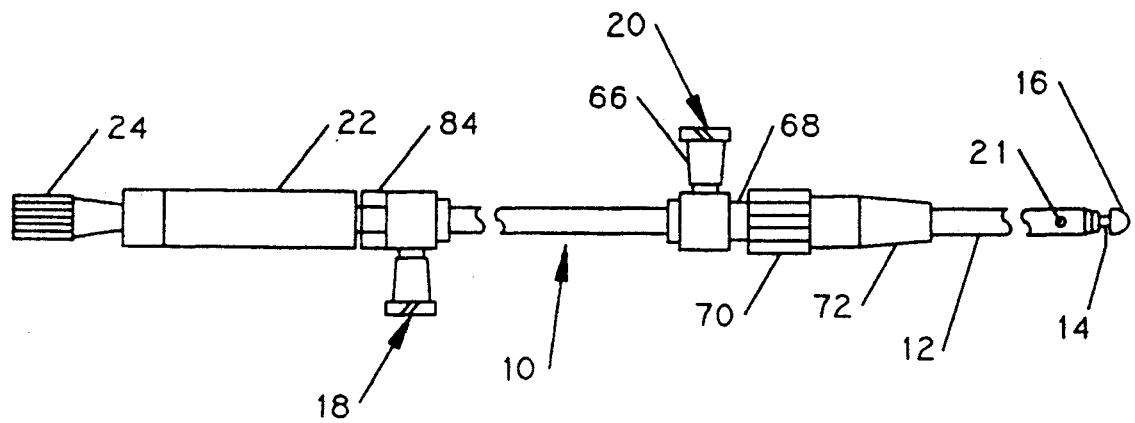
FIG. 1 is a schematic plan view of an embodiment of the present invention.

Thus there is shown in FIG. 1 a schematic plan view showing the major components of an apparatus, catheter, assembly, device or article 10 of the present invention. In this embodiment of the invention, apparatus 10 comprises a flexible, tubular sleeve or catheter body 12 having distal and proximal ends. The distal end of sleeve 12 is the right-most, or working portion of the device depicted in FIG. 1. Generally speaking, "the distal end" of sleeve 12 is that portion of sleeve 12 in the vicinity of any vessel obstruction which is to be removed by operation of an apparatus of this invention. Sleeve 12 (and the catheter) may be up to several feet in length, depending upon the distance between the vessel obstruction, the site where the catheter enters the body, and the distance to any required external fluid management systems.

As is described in greater detail below, running through sleeve 12 is a drive means. Drive means, in one embodiment comprises a torquable, flexible, drive cable 14 which is rapidly rotatable, and at least partially steerable or pushable. Fixedly attached to drive cable 14 so as to be rapidly rotated thereby is a head means or a tip. In this embodiment, the head means 16 comprises a substantially solid, preferably metal, tip or head 16 which tapers to a turbulence generating means (not depicted in FIG. 1) located between the distal end of sleeve 12 and head 16. (A preferred turbulence generating means is more completely described below.) Drive cable 14 is the means by which the head means of this invention is rapidly rotated.

Also shown in FIG. 1 is a fluid input port 18 which is a portion of the fluid delivery means. (Fluid output ports are located adjacent the turbulence generating means substantially coaxial with sleeve 12 and are not depicted in FIG. 1.) Aspiration output port 20 is a part of the fluid and debris recovery means, further details of which are included below. Aspiration output port 20 is connected (by means of an interior channel) to aspiration input port 21 which is located adjacent the turbulence generating means. In this preferred configuration, aspiration input port 21 is located and extends through the wall of sleeve 12. A plurality or multiplicity of aspiration input ports are within the contemplation of this invention. Rotatable fluid seal 22 permits rapid rotation of drive cable 14 within sleeve 12 while the drive cable is coupled to an external source of rotational energy (not shown) such as an electric motor or a source of compressed air. Drive cable 14 of catheter 10 would normally be connected to an external electric motor by means of, for example, a flexible coupling 24. Drive means or cable 14 runs through the entire length of catheter 10 and is substantially coaxial therewith.

Figure 2:
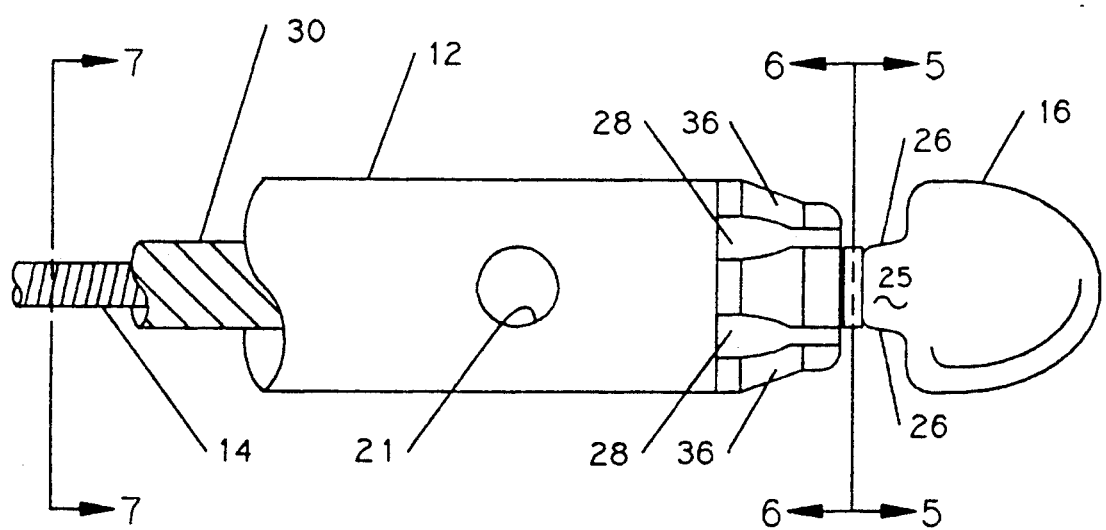
FIG. 2 is an enlarged fragmentary view of the tip segment or distal end of the embodiment of the invention shown in FIG. 1.

FIG. 2 is an enlarged fragmentary view of the tip segment or portion of the apparatus shown in FIG. 1 with parts cut away. As shown, the distal end of sleeve 12 has bulbous head 16 projecting therefrom. As shown, head 16 is substantially smooth i.e., having no cutting or shearing structure intended physically to cut or erode an obstruction were it to come into contact therewith. Between head 16 and sleeve 12, at the base or neck 25 of the head, is a turbulence generating means which, in this embodiment, comprises flats or facets 26. Head 16 tapers or "necks down" to create and define flats or facets 26.

Facets are a preferred turbulence generating means of this invention. However, many other possible configurations at the neck or base of head 16 could be employed to create turbulence. For example, head 16 could be hollow, cone-shaped, or of a mushroom configuration. The "stem" of a mushroom-shaped head would then be connected to the drive means to permit rapid head rotation. Within and protected by the mushroom "head" would be an interior space in which radial turbulence generating blades, bins, facets, or other projections could be located.

Drive cable 14 projects coaxially through sleeve 12 and is fixedly attached to head 16 so as to permit head 16 to be rapidly rotated thereby. Output ports 28 project through bushing housing 36, the arrangement of which is discussed below. Output ports 28 direct fluid output longitudinally toward flats 26 to generate a particularly preferred thrombus dissolution zone.

Sidewall aspiration input port 21 is shown in FIG. 2. A second pair of end-disposed aspiration input ports 28 also are illustrated. As long as either end-disposed or side wall aspiration input ports are provided, it is largely a matter of design discretion which is utilized. Sidewall and end or end-disposed aspiration input ports, if both are employed, would preferably be in fluid communication with each other and ultimately (via an interior channel) with aspiration output port 20.

Figure 4:
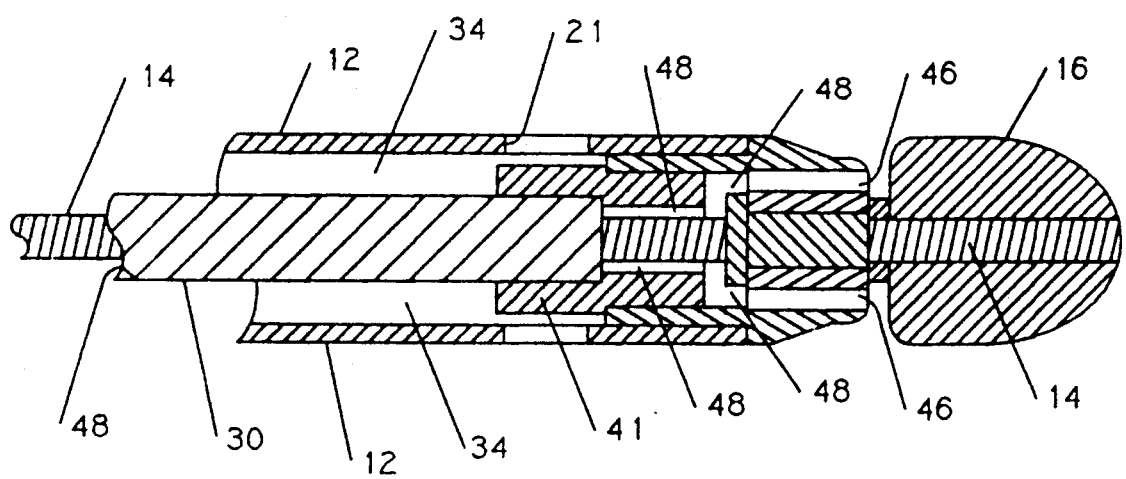
FIG. 4 is a view along the line of that of FIG. 3 rotated 45 degrees.

Also shown in FIG. 2 is a flexible inner member fluid delivery or fluid containment tube or lumen 30. Fluid delivery tube 30 is part of the fluid delivery means which includes fluid input port 18. The details of the fluid connection between fluid delivery tube 30 and fluid input port 18 are illustrated in FIG. 4. In FIG. 2, fluid delivery tube 30, drive cable 14, and sleeve 12 are all substantially coaxial. While not required, it has been found that coaxial construction tends to be the most space efficient, providing the smallest diameter catheter.

Figure 3:
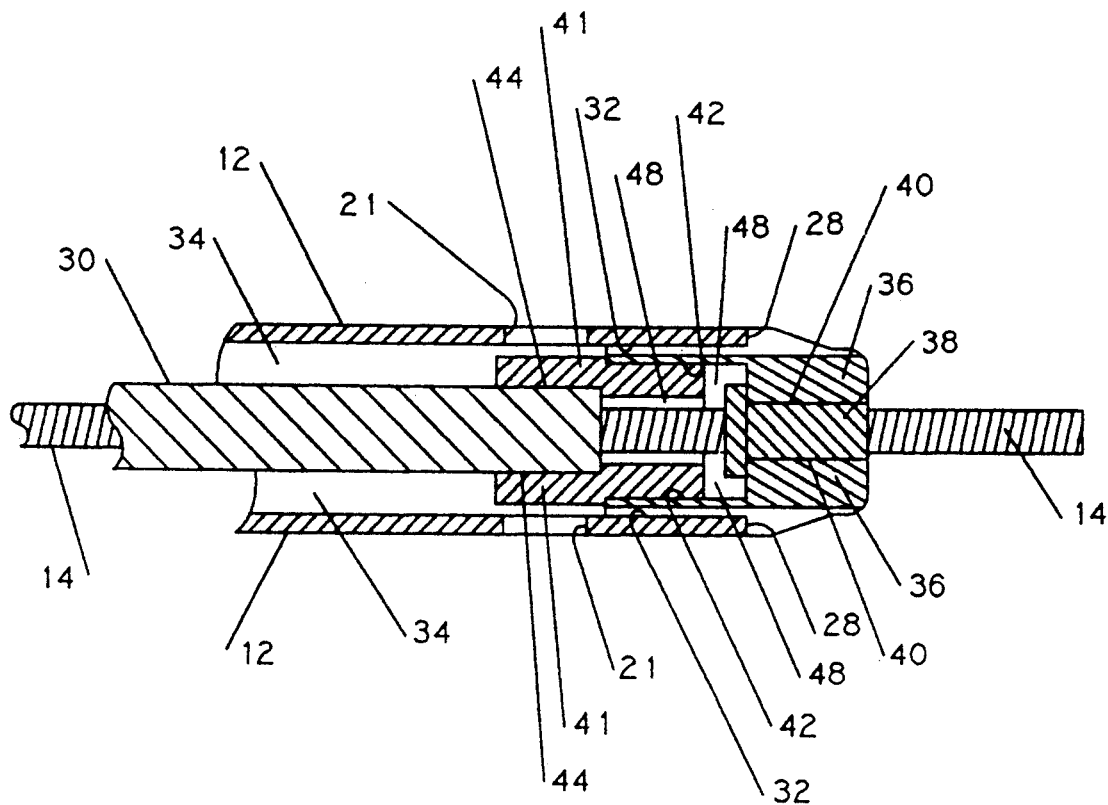
FIG. 3 is a sectional view of the device of FIG. 2 taken along line 2—2.

FIG. 3 is a partial section view of the device of FIG. 2 taken along line 2—2. For purposes of clarity, head 16 (shown in other views) has been removed. Side wall aspiration input port 21 is shown to be in communication (via distal aspiration channel segment 32) with end-disposed aspiration port 28. Aspiration ports 21, 28 and distal channel segment 32 are in fluid communication with medial aspiration channel segment 34. Medial aspiration channel segment 34 is in downstream fluid communication with aspiration output port 20. Shown in FIG. 3 is bushing housing 36 which cooperates with headed bushing 38 to permit drive cable 14 to rotate (on bearing surface 40). Bushing housing 36 is mounted on adaptor sleeve or lumen sleeve 41 at adaptor surface 42. Lumen sleeve 41 is, in turn, mounted on inner lumen or tube 30 at inner lumen surface 44. With this configuration, rapid rotation of drive cable 14 within coaxial inner lumen 30 is permitted.

FIG. 4 depicts an article of FIG. 3 in partial section, but rotated 45 degrees from the view of FIG. 3 to show more detail of the fluid and debris recovery means. Fluid output port 46 communicates with distal fluid channel segment 48 and with the channel within. Fluid delivered through inner lumen 30 to distal fluid channel 48 is delivered adjacent head 16 from output ports 46. The channel defined by inner lumen 30 is in fluid communication with fluid input port 18 on the proximal end of the apparatus.

Figure 5:
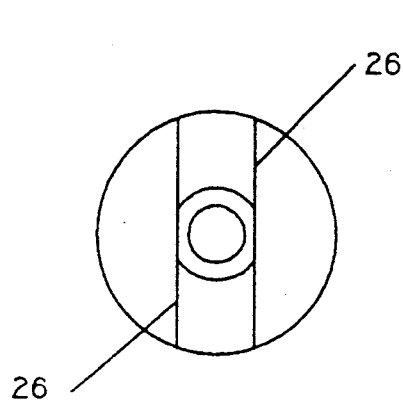
FIG. 5 and 5A are view of the device taken along line 5—5 of FIG. 2.
Figure 5A:
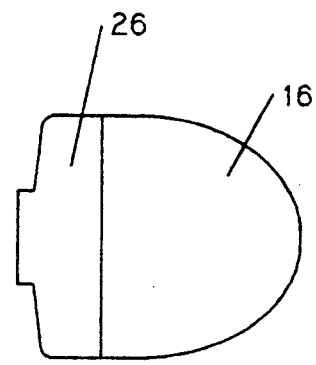

FIGS. 5 and 5A are views of a head means of the device taken along line 5—5 of FIG. 2. Flats or facets 26, which merge with bulbous, ellipsoidal, smooth, substantially spherical or bullet-shaped head 16 are clearly shown. Flats 25 do not project beyond the circumferential profile of head 16. Flats 26 generate a particularly advantageous turbulence (for removing vessel obstructions) in conjunction with pressurized fluid axially or longitudinally emitting or delivered from fluid delivery ports 46 (such as are shown in FIG. 4). Fluid axially directed upon rotating flats 26 creates a preferred thrombus obstruction or dissolution zone. The capability of controlled delivery of fluid to the turbulence generating means while it is in rapid rotation is a particular advantage of this invention. By adjustment of fluid pressure and rotation speed, it may be possible to adjust or to customize the turbulence zone or thrombus destruction zone to the type of vascular obstruction to be removed.

Figure 6:
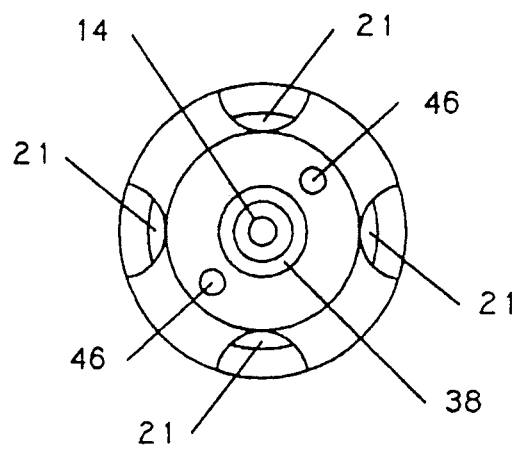
FIG. 6 is a view of the device taken along line 6—6 of FIG. 2.

FIG. 6 is a view of the device taken along line 6—6 of FIG. 2. Fluid output ports 46 are shown in relation to aspiration input ports 21. Fluid emitting or emerging from the apparatus would exit ports 46 essentially perpendicularly to the plane of FIG. 6. Headed bushing 38 is shown to be mounted upon guide wire 14.

Figure 7:
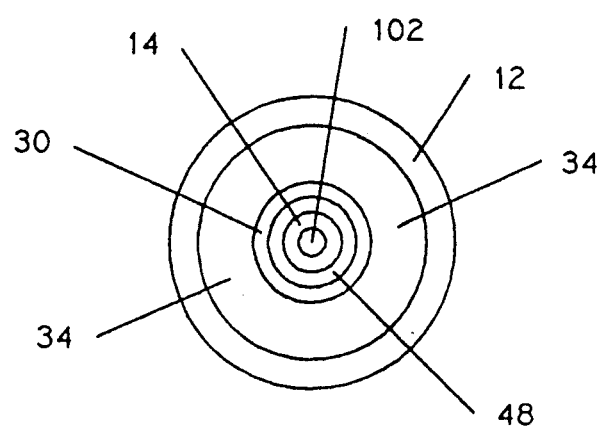
FIG. 7 is a cross sectional view of the device illustrating the cross sectional relationships between the various coaxial components.

FIG. 7 is a cross sectional view of the device illustrating the schematic relationship between the various coaxial components. Sleeve, outer wall, or exterior sheath 12 is coaxial with inner tube, inner fluid tube or lumen 30. Between the outer sheath (or outer tube) 12 and inner lumen 30 is aspiration channel 34. Within aspiration channel 34 is drive cable or drive wire 14 which then defines fluid delivery channel 48. Liquids or fluids in fluid delivery channel 48 and fluids and debris in aspiration channel 34 (in operation of the device) would be proceeding in opposite directions if the fluid output means and the fluid input means were simultaneously operated. Drive cable 14 optionally may be hollow, leaving an inner most channel or lumen 102 into which a guide wire could be slid.

Figure 8:
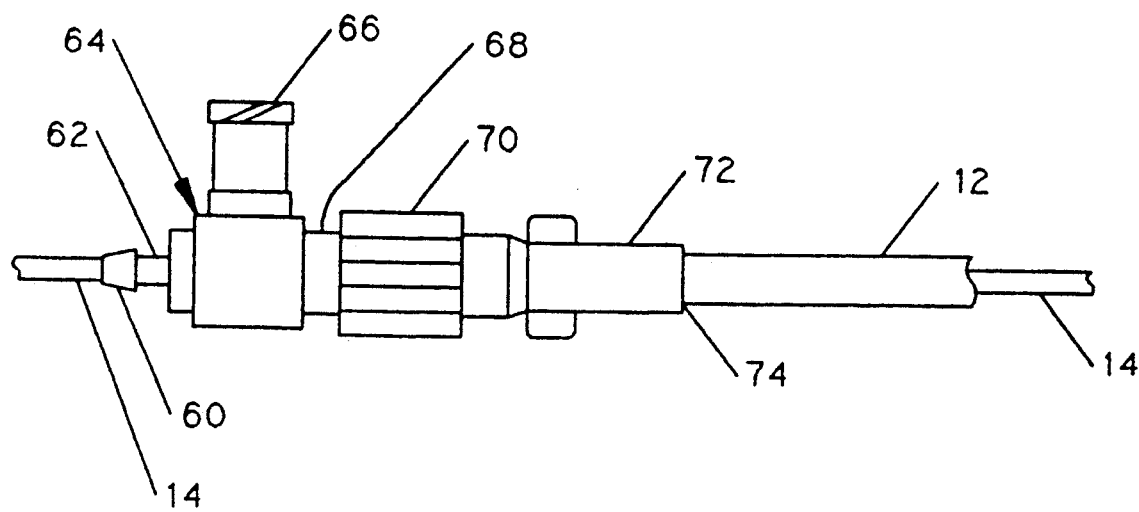
FIG. 8 is a detailed depiction of the aspiration output port assembly generally indicated in FIG. 1.

FIG. 8 shows in detail the features of the aspiration output port assembly, as shown generally at arrow 20 in FIG. 1. The particular details are not critical to the invention, there being a number of design alternatives which would be within the skill of one familiar with this art. As described above, drive cable 14 proceeds through the illustrated portion of the apparatus substantially coaxially with sleeve 12. Sleeve 12 comprises a flexible, Hytrel polyester material preferably having a wall thickness in the range of about 0.008 in. to 0.012 in. As is more completely discussed below, the overall diameter of sleeve 12 will largely be determined by the size of the vessel into which the device is to be inserted. It is a general design preference that the portion of the catheter to be inserted in a vessel have the smallest overall diameter or profile consistent with its intended function.

Proceeding from the left of FIG. 8, there is shown a barb fitting 60. Barb fitting 60 is bonded to junction block or header 64 on tube segment 62. Barb fitting 60 is not seen in FIG. 1 because it is compressed within sleeve 12 to permit connection of the aspiration output port assembly to the body of the catheter. Junction block 64 is in fluid communication with the interior of sleeve 12 so as to permit fluid and thrombus destruction products or debris to be removed, therefrom, e.g., by aspiration. Junction block 64 connects through female luer 66, to an external source of vacuum (e.g., an aspirator) of sufficient strength to withdraw fluid and material from the device. By means of a male luer 68, back ring 70 and female luer lock adaptor 72 (and adhesive at 74) junction block 64 provides a vacuum and fluid tight access to medial portion or segment 34 and distal portion or segment 32 (shown in FIG. 3) of the aspiration channel.

Figure 9:
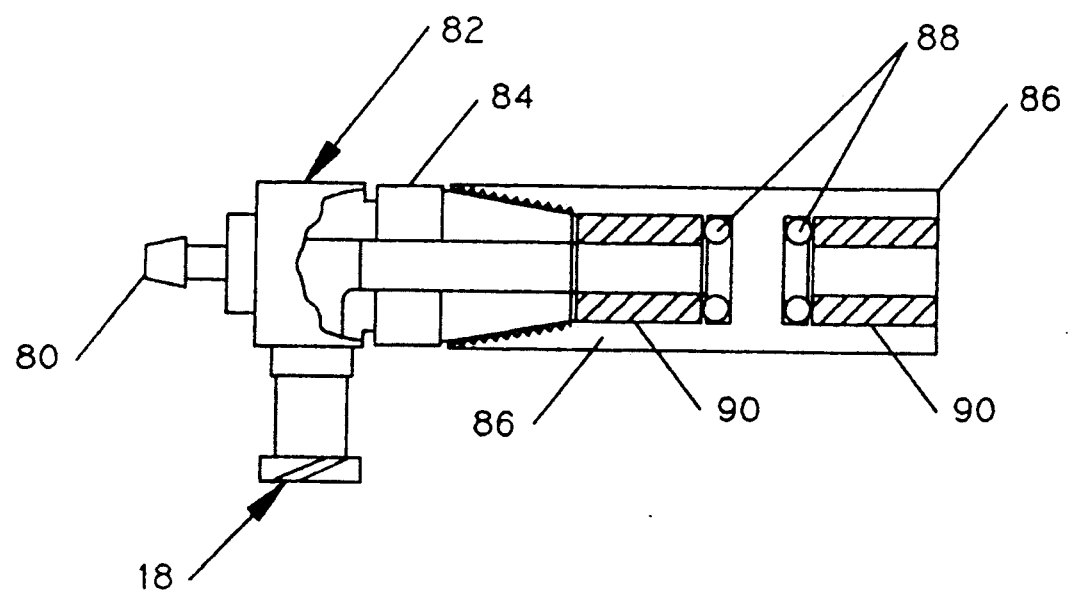
FIG. 9 is a partial section view of a fluid injection assembly also generally depicted in FIG. 1.

FIG. 9 shows, in partial section, the details of fluid input or fluid injection port generally designated 18 in FIG. 1. As with the aspiration output port assembly of FIG. 8, a second barb valve 80 is connected to a second junction block or header 82. Junction block 82 (via threaded fitting 84) is in fluid communication with housing 86. Within housing 86 are "O" rings 88 which are held in place by "Teflon" polymer bearings 90. External fluid access to junction block 82 is by means of fluid input port 18.

The assembly of FIG. 9 permits fluid to be introduced around drive cable 14 (not shown) while permitting the drive cable to rotate. The plurality of "O" ring assemblies are used to decrease the likelihood that fluid would enter the catheter (at 18) and exit toward an external motor (not depicted) employed to rotate drive cable 14.

In FIG. 1, the assemblies of FIGS. 8 and 9 are shown to be separated by a segment of the catheter. One design alternative would be for these two assemblies to be placed next to each other, possibly in contact. In yet another embodiment, a single junction block manifold, or header could be employed to provide fluid and aspiration access to the respective channels of the catheter. Such a junction block or header would require separate fluid input and aspiration output ports in fluid communication with their respective channels within the tubular body of the catheter.

Figure 10:
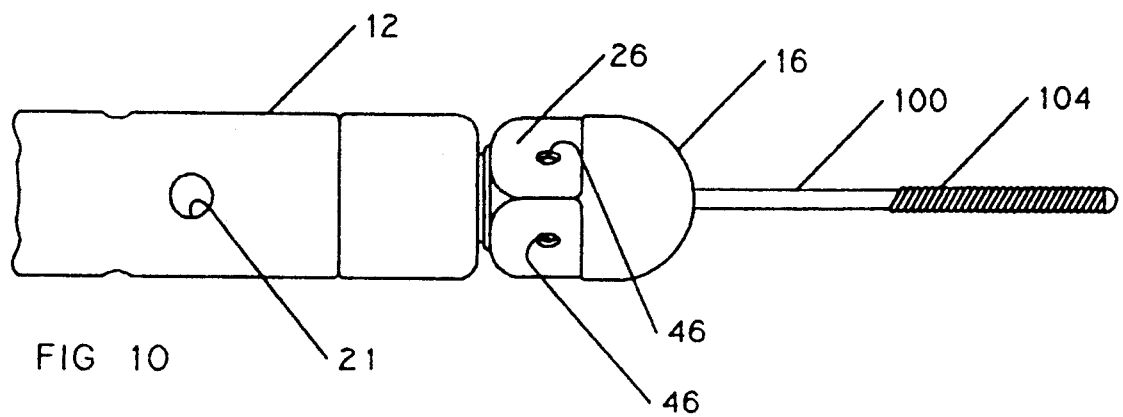
FIG. 10 is an embodiment of the present invention employing a non-removable guide wire.
Figure 11:
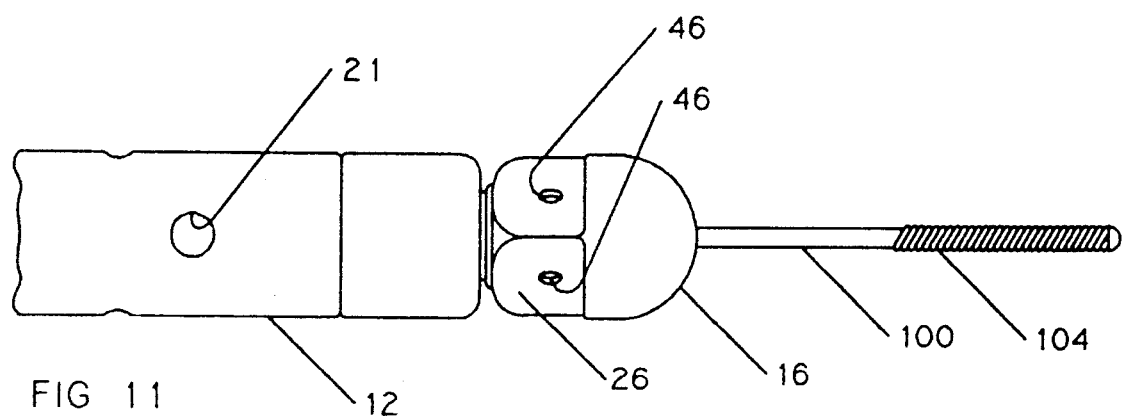
FIG. 11 is an embodiment such as in FIG. 10 employing a removable guide wire.

FIGS. 10 and 11 depict an apparatus of this invention employing an optional guide means such as a guide wire 100. Guide wire 100 would project through the inner most or center lumen of the apparatus shown at 102 in FIG. 7. Guide wire 100 terminates in a radiopaque, atraumatic coil 104. By means of fluroscopy, atraumatic, radiopaque coil 104 is used to steer the guide wire to the point where its distal end, tip, or head is located immediately adjacent the site of a previously identified thrombus. Guide wire 100 generally would have an outside diameter in the range of approximately 0.008 to 0.016 inches. With such a small diameter relative to the average vessel diameter, the guide wire is very capable of following or being steered through the tortuous path of body vessels to the site of an obstruction. The two embodiments of FIGS. 10 and 11 differ primarily in that coil 104 in FIG. 10 is of a slightly larger diameter than center lumen 102 in head 16. The guide wire up to tip 104 is generally a solid core material. The material of guide wire 100 would be sufficiently flexible as well as sufficiently stiff to permit the rest of a catheter of the invention to track over it once the guide wire has been advanced to, or possible through, the obstruction or stenosis site.

A preferred guide wire for use with a catheter of this invention is commercially available from the Lake Region Manufacturing Company, Inc. of Chaska, Minn. under the trade designation ONTRAC ™. After the catheter has been directed to the site of the stenosis, the guide wire shown in FIG. 11 optionally may be withdrawn, leaving the catheter in place next to the obstruction. Alternatively, the guide wire may be left in place with the catheter slidably or rotatively disposed thereover. This is shown in FIG. 10. Of particular note is the fact that, in this embodiment, fluid output ports 46 are shown to be disposed on turbulence generating means or flats 26. In other words, fluid can be delivered from the face of the flats 26. Aspiration input port 21 is shown to be disposed in the side wall of flexible sleeve 12.

Figure 12:
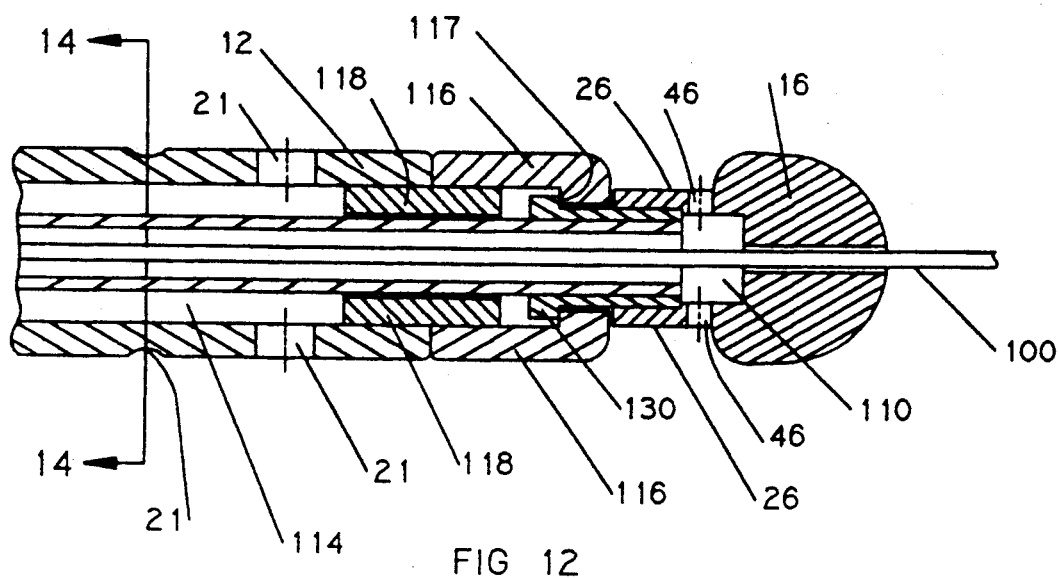
FIG. 12 is a cross-section view of an apparatus such as that shown in FIG. 11.

FIG. 12 shows a partial-section view of an apparatus of FIGS. 10 or 11. FIG. 12 is a depiction of the device disposed along a guide wire 100. Guide wire 100 extends coaxially through the catheter which is coaxially moveable therealong. Fluid output ports 46 are also disposed in flats 26 in this embodiment. Fluid output ports 46 communicate with a header 110 which is located interiorly in head or bulb 16. Header 110 communicates with internal channel or lumen 112 which would, itself, be in fluid communication with an external source of fluid via input port 18. Aspiration input ports 21 are disposed in the side wall of tube or lumen 12. Aspiration input ports 21 communicate with channel 114 and also provide access to an external source of fluid. In this example, channel 114 would communicate with, for example, an aspirator connected to aspiration output 20. The internal structure in FIG. 12 shows a sleeve cap affixed to an internal sleeve 118. Sleeve 118 is bonded to the inside distal end of lead body 12. Headed bushing 130 is interiorly affixed to head 16 and to drive means 14 thereby permitting rapid rotation of head 16. Head 16 is prevented from precessing in this arrangement. Bushing 130 is held in place by the inside abutment surface 117 of sleeve cap 116.

Figure 13:
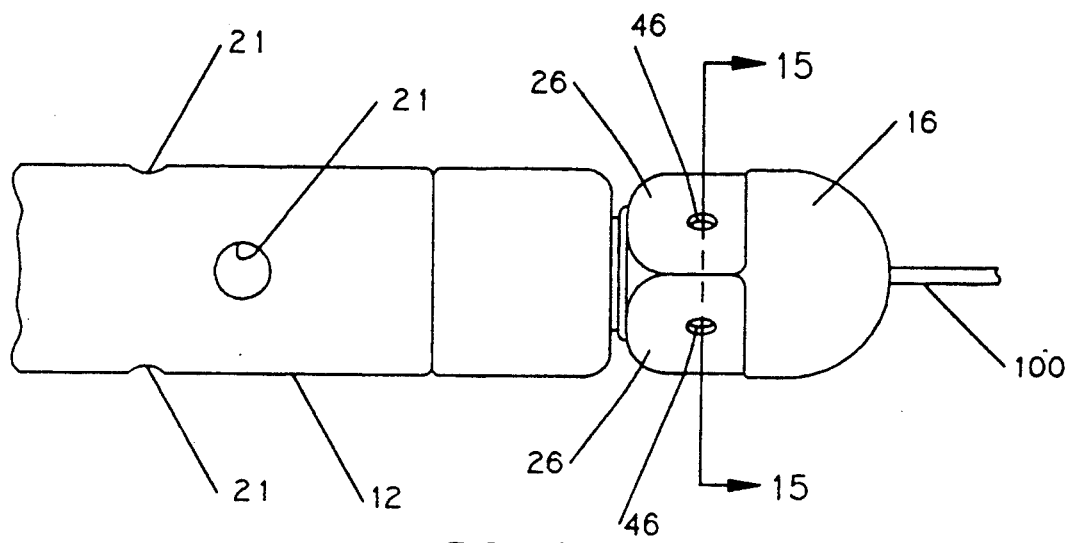
FIG. 13 is the apparatus shown in FIG. 12 but rotated approximately 45° from the section view shown in FIG. 12.

FIG. 13 shows the exterior details of the device shown in FIG. 12.

Figure 14:
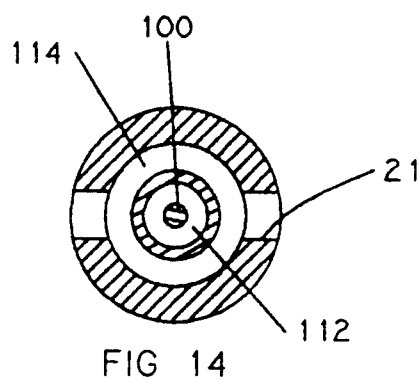
FIG. 14 is a cross-sectional view taken along line 14—14 of FIG. 12.
Figure 15:
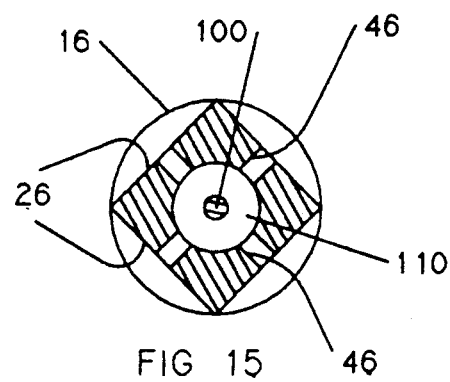
FIG. 15 is a cross-sectional view taken along line 15—15 of FIG. 13.
Figure 16:
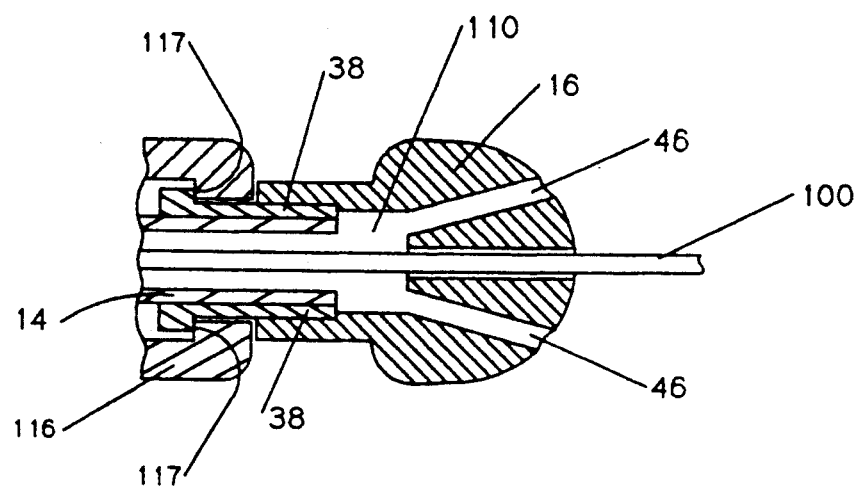
FIG. 16 is a cross-sectional detailed view of an alternative embodiment of the head of nose of the present invention.

FIG. 14 is a sectional view of the apparatus of FIG. 12 taken along line 14—14. FIG. 14 shows the arrangement of channels 112 and 114 and of aspiration input ports 21. FIG. 16 shows a sectional view of the apparatus of FIG. 13 taken along line 15—15. Disposed in flats 26 are fluid output ports 46 which are, in turn, in communication with header 110. Header 110 is interiorly disposed in bulb 116. Thus, liquids emitting from fluid output ports 46 create additional turbulence in conjunction with facets 26 so as to enhance the overall thrombus dissolution performance of the apparatus.

FIG. 16 is yet a further embodiment of the present invention wherein fluid output ports 46, rather than being substantially perpendicular to the axis of the apparatus, are obliquely disposed with respect thereto. FIG. 16 suggests that the precise angle of fluid delivery from fluid output ports 46 and the axis of the apparatus is not critical. Thus, by means of a header, fluid output ports 46 could, in fact, be directed toward the catheter body (i.e., toward the left in FIG. 16) of the apparatus). Head 16 is mounted on headed bushing 38 which rotates against the inside abutment 117 of sleeve cap 116. In this manner, fluids are permitted to course through header 110 and out fluid output channels or parts 46. Head 16 is then turned by drive means or drive cable 14 as is clearly shown in FIG. 16.

Figure 17:
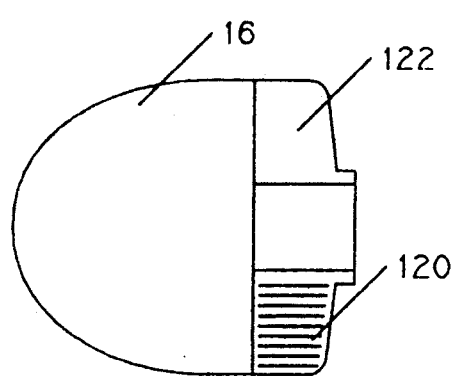
FIGS. 17 and 18 are side and axial views of alternative turbulence generating means of the present invention.
Figure 18:
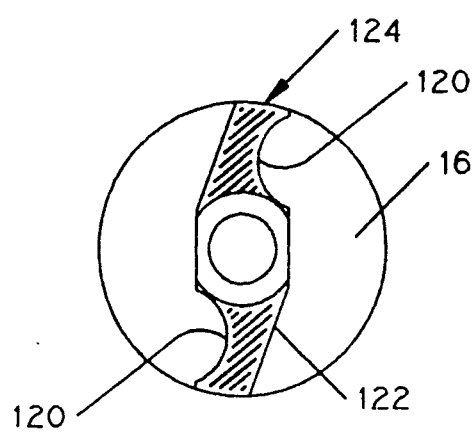

FIGS. 17 and 18 are side views and end views of alternative turbulence generating means of the invention. Rather than employing flats or four faces, as shown in FIGS. 10 and 11, arcuate leading surfaces 120 and obliquely angled following surfaces 122 are disposed on an impeller 124. Impeller 124, as depicted, generates a particularly advantages turbulence for thrombus dissolution. Rotation of the tip or bulbous head depicted in FIGS. 17 and 18 would be generally clockwise when viewed as in FIG. 18.

Figure 19:
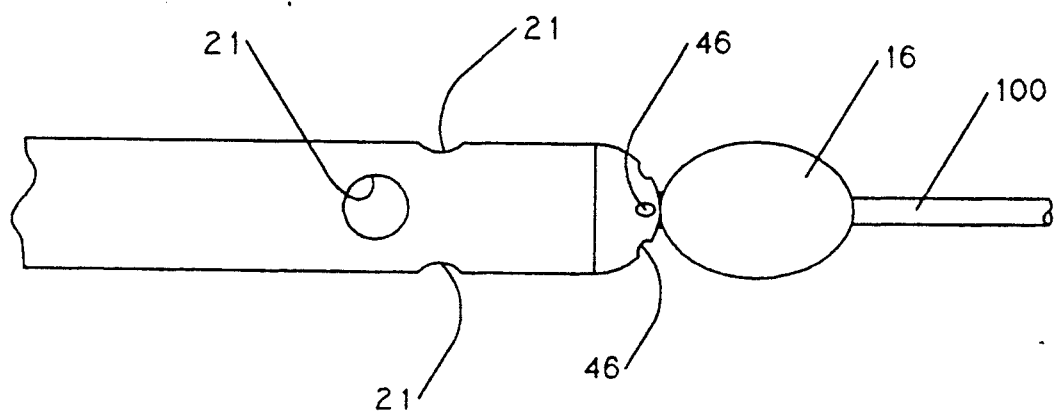
FIGS. 19 and 20 are side plan views of the distal portion of further embodiments of catheters of the present invention.
Figure 20:
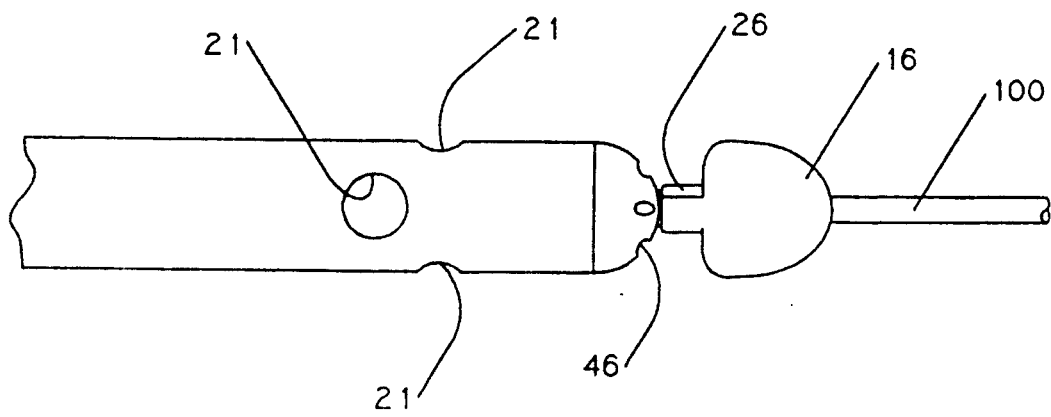

FIGS. 19 and 20 depict further embodiments of this invention. Head 16 in FIG. 20 is rotated 90° from that of FIG. 19 to show flats 26. The rounded configuration of head 26 is particularly suitable for withdrawing the catheter from a vessel.

For the most part, the components for the present apparatus or assembly will be machined from a thermosetting or thermoplastic material. Tip or head components generally are made of metal, stainless steel being preferred luer adapters and related parts may comprise a polycarbonate material. Many other sufficiently rigid, polymeric materials may be employed.

The preferred drive cable of the present invention is a multifilar, double layer torque cable commercially available from Lake Region Manufacturing Company of Chaska, Minn. Generally, the qualifications for a drive cable are that it be torquable to rotate tip or head, rapidly rotatable, and that it be of sufficiently narrow diameter, so as to permit the device to be used in small vessels. It is, of course, important that the drive cable employed efficiently transfer rotational torque from its proximal end to the distal end or tip end. Efficient transfer of rotational torque means that the maximum turbulence would be created adjacent the distal end or tip of the apparatus. Other commercially available drive cables or drive wires may be employed in this invention.

The inner member or inner lumen 30 of the present invention preferably comprises a braided polyimide tubing material such as that commercially available from the HV Technologies Company of Trenton, Ga. The braided configuration of this preferred inner lumen material permits a very thin walled lumen to be employed which has sufficient strength and flexibility to permit pressurized fluids to be passed therethrough. The wall of the braided polyimide inner member optionally be reinforced with a braided stainless steel structure having a wall thickness of about 0.0035 inches. The optional stainless steel reinforcement permits liquids of a higher pressure to be deployed through the inner lumen to fluid output ports, e.g., 46.

In operation, a pressurized fluid is injected or pumped from an external source through input port 18. Passing through junction block 82 to inner lumen 30, the pressurized fluid passes down the fluid channel 48 to exit at fluid output port 46. Fluids emerging from output ports 46 encounter flats 26 at the base of head 16 as head 16 is rotated via drive cable 14. In this manner, a pulsatile effect is imparted to the fluids emerging from the body of the catheter. Surprisingly and unexpectedly, this pulsatile turbulence effect is believed to dramatically enhance the ability of the present apparatus to remove vessel obstructions such as thrombi.

It is known in the art to which this invention pertains that, the destruction products and debris of vessel or vascular occlusions or obstructions generally should not be permitted to proceed down the vascular stream. In a practice of the present invention, obstruction debris is prevented from proceeding downstream from the catheter by adjustment of the rates of fluid input and of fluid and debris removal. Essentially, the rate of aspiration of fluid and debris from the site of obstruction is coordinated with the rate of fluid input so that particulate material and debris are contemporaneously removed from the obstruction site as they are generated. By this expedient, the downstream flow of debris generated from destruction of the occlusion is controlled.

It is contemplated that a selection of sizes of the present catheter will be employed, depending upon the size of the vessel from which the occlusion is to be removed. Generally speaking, the diameter of the catheter should be approximately two-thirds of the diameter of the vessel in which it is to be inserted. An exemplary sized catheter, such as those depicted in the figures, is about 7.5 French. For coronary applications, an over-the-wire catheter, i.e., a catheter using a guide wire, would have a maximum diameter in the range of 6 F.

The apparatus of this invention is not a cutting device in the sense that mechanical cutting or shear forces are used to effect thrombus dissolution. Generally speaking, the rotatable head will be substantially smooth. Moreover, in a preferred practice of the present invention, the device can be employed to remove a vessel obstruction with little more than incidental contact between the device and the occlusion. It is the feature which permits the present invention substantially to enhance occlusion dissolution without substantially increasing the likelihood of damaging the vessel wall.

The above disclosure will suggest many alterations and variations to one of ordinary skill in this art. This disclosure is intended to be illustrative and not exhaustive. All such variations and permutations suggested by the above disclosure are to be included within the scope of the attached claims.

What is claimed is as follows:

1. A catheter for removing an obstruction in a vessel of a patient, said catheter comprising:
   a flexible, tubular sleeve having distal and proximal ends, said sleeve having extending substantially coaxially therethrough so as to project therefrom;
   drive means, said drive means being flexible and rotatable, and having fixedly mounted on its projecting end;
   head means, said head means comprising a bulbous head, said head being mounted on said drive means so as to be rotated thereby, said head means further including;
   a turbulence generating means, said turbulence generating means being disposed between said distal end of said sleeve and said head so as to create turbulence when said drive means is rotated, said catheter further comprising:
   means for delivering fluid proximate the distal end of said sleeve, and
   means for recovering fluid and debris from proximate the proximal end of said sleeve.

2. A catheter according to claim 1 wherein the drive means comprises a hollow drive cable.

3. A catheter according to claim 1 wherein the head is substantially hemispherical and is hollow.

4. A catheter according to claim 1 wherein the turbulence generating means is a plurality of facets.

5. A catheter according to claim 4 wherein the head has a base on which it is mounted and the turbulence generating means comprises a plurality of facets, the planes of which are substantially parallel, the facets being located on opposite sides of the axis of the drive means, said facets being defined by the base.

6. A catheter according to claim 1 wherein the head means comprises a substantially hollow cone, the cone having therein an axially disposed stem on which the cone is interiorly mounted and by which the head means may be rotated, said turbulence generating means being mounted within said cone.

7. A catheter according to claim 6 wherein the cone is a nose cone and the turbulence generating means is a plurality of radial projections.

8. A catheter according to claim 7 wherein the projections are fins.

9. An apparatus according to claim 1 which further comprises guide means, said guide means extending substantially coaxially through the catheter.

10. An apparatus according to claim 1 wherein the means for delivering fluid comprises a lumen which is in fluid communication with the proximal end of the sleeve and a fluid delivery port located proximate the turbulence generating means.

11. An apparatus according to claim 1 wherein the fluid and debris recovery means comprises a second lumen which is in fluid communication with a fluid and debris recovery port and the proximal end of the sleeve.

12. An apparatus according to claim 1 in which the fluid delivery means comprises an inner lumen in communication with a fluid delivery port and the proximal end of the catheter and the fluid recovery means comprises an outer lumen in communication with a fluid recovery port and the proximal end of the sleeve, the inner and outer lumens being coaxial.

13. An apparatus according to claim 12 wherein the drive means, the inner lumen, and the outer lumen are all substantially coaxial for at least a substantial length of the catheter.

14. An apparatus of claim 1 which further comprises external means to provide rotational energy to the drive means.

15. An apparatus of claim 1 which further comprises external fluid input means and removal means.

16. A catheter for removing an obstruction in a vessel of a patient, said catheter comprising:
 a flexible, tubular sleeve having distal and proximal ends, said sleeve having extending substantially coaxially therethrough;
 a drive cable, said drive cable being flexible and rotatable, and having fixedly mounted thereon;
 a bulbous head, said head having a neck and being mounted on said drive cable by said neck so as to be rotated thereby, said head including;
 a plurality of facets defined by said neck, the facets being disposed between said distal end of said sleeve and said head so as to create turbulence when said drive means is rotated, said catheter further comprising:
 fluid delivery ports located proximate the distal end of said sleeve, the fluid delivery ports comprising a coupled lumen and a fluid input port so that said fluid delivery port can be coupled to an external source of fluid;
 fluid and debris recovery ports located proximate the distal end of said sleeve the fluid recovery port comprising a coupled lumen and a vacuum output port so that said fluid recovery port can be coupled to an external source of vacuum;
 wherein said lumens, said drive cable, and said sleeve are all substantially coaxial through at least a substantial length of the catheter.

17. A catheter according to claim 16 wherein the drive cable is hollow.

18. A catheter according to claim 17 which further includes a guide means inserted within said drive cable.

19. A method for removing an obstruction in a body vessel comprising the steps of:
 identifying the site of the obstruction;
 providing a catheter comprising:
  a flexible, tubular sleeve having distal and proximal ends, said sleeve having extending substantially coaxially therethrough so as to project therefrom;
  drive means, said drive means being flexible and rotatable, having fixedly mounted on its projecting end;
  head means, said head means comprising a bulbous head, said head being mounted on said drive means so as to be rotated thereby, said head means further including;
  turbulence generating means, said turbulence generating means being disposed between said distal end of said sleeve and said head so as to create turbulence when said drive means is rotated, said catheter further comprising;
  means for delivering fluid proximate to the distal end of said sleeve, and
  means for recovering fluid and debris from proximate the proximal end of said sleeve;
 directing the head means through the body vessel to a location adjacent the obstruction;
 rapidly rotating the drive means to create turbulence proximate the obstruction while simultaneously delivering fluid proximate the obstruction site and removing fluid from proximate the obstruction site until the obstruction is removed.

20. A method according to claim 19 wherein the fluid is delivered proximate the obstruction in a pulsatile fashion.

21. A method according to claim 19 wherein the fluid is delivered in the vicinity of the turbulence generating means.

22. A method according to claim 19 wherein the fluid is delivered so as to impinge upon the turbulence generating means.

23. A method according to claim 19 wherein the directing step is accomplished by inserting a guide wire to a location near the obstruction, and sliding the catheter over the guide wire until the distal end of the catheter is near the obstruction.

24. A method for removing an obstruction in a body vessel comprising the step of:
 generating a zone of turbulence in the vicinity of the obstruction by rapid rotation of a turbulence generating means comprising a plurality of rotatable facets while delivering pressurized fluid to the zone of turbulence and recovering fluid and debris produced from the obstruction by the turbulence.

25. A method according to claim 24 wherein fluid delivery and fluid recovery are accomplished simultaneously.

26. A method according to claim 24 wherein fluid delivery and fluid and debris recovery are accomplished sequentially.

27. A method according to claim 24 wherein the obstruction is removed from the vessel without physical contact between the turbulence generating means and the obstruction.

28. A method according to claim 24 wherein the pressurized fluid is delivered so as to impinge upon said facets.

29. A method according to claim 24 wherein the zone of turbulence is generated in a pulsatile fashion.

30. A method according to claim 29 wherein the zone of turbulence is generated by intermittently delivering fluid to the zone of turbulence while activating the turbulence generating means.

31. A catheter for removing an obstruction in a body vessel comprising:
 a flexible, tubular sleeve having distal and proximal ends, said sleeve having extending substantially coaxially therethrough so as to project therefrom;
 drive means, said drive means being flexible and rotatable, having fixedly mounted on its projecting end;

head means, said head means comprising a bulbous head, said head being mounted on said drive means so as to be rotated thereby, said head means further including;

turbulence generating means disposed between the distal end of said sleeve and said head, said catheter further comprising;

means for delivering fluid proximate to the distal end of said sleeve, and means for recovering fluid and debris from proximate the proximal end of said sleeve.

32. A catheter according to claim 31 wherein the turbulence generating means is a plurality of facets on said head.

33. A catheter according to claim 31 wherein the means for delivering fluid includes ports in the head means.

34. A catheter according to claim 33 wherein the ports in the head means are defined by the turbulence generating means.

* * * * *